US010695572B2

(12) United States Patent
Maile et al.

(10) Patent No.: US 10,695,572 B2
(45) Date of Patent: Jun. 30, 2020

(54) SYSTEM FOR RECHARGING A RECHARGEABLE IMPLANTABLE MEDICAL DEVICE INCLUDING AN IMPLANTABLE RECHARGING BRIDGE

(71) Applicant: CARDIAC PACEMAKERS, INC., St. Paul, MN (US)

(72) Inventors: Keith R. Maile, New Brighton, MN (US); Jacob M. Ludwig, Isanti, MN (US); William J. Linder, Golden Valley, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 184 days.

(21) Appl. No.: 15/940,481

(22) Filed: Mar. 29, 2018

(65) Prior Publication Data

US 2018/0280706 A1  Oct. 4, 2018

Related U.S. Application Data

(60) Provisional application No. 62/480,772, filed on Apr. 3, 2017.

(51) Int. Cl.
*A61N 1/372* (2006.01)
*A61N 1/378* (2006.01)
(Continued)

(52) U.S. Cl.
CPC ......... *A61N 1/3787* (2013.01); *A61N 1/3756* (2013.01); *A61N 1/37211* (2013.01);
(Continued)

(58) Field of Classification Search
CPC ...... A61N 1/205; A61N 1/0587; A61N 1/362; A61N 1/372; A61N 1/37205;
(Continued)

(56) References Cited

U.S. PATENT DOCUMENTS 5,383,915 A * 1/1995 Adams ............... A61N 1/37282
128/903
5,626,630 A * 5/1997 Markowitz .......... A61B 5/0031
128/903

(Continued)

FOREIGN PATENT DOCUMENTS

WO  2013040549 A1  3/2013
WO  2017165093 A1  9/2017

OTHER PUBLICATIONS

International Search Report and Written Opinion for Application No. PCT/US2018/02230, 13 pages, dated Jun. 11, 2018.
(Continued)

*Primary Examiner* — Eugene T Wu
(74) *Attorney, Agent, or Firm* — Seager, Tufte & Wickhem LLP

(57) ABSTRACT

A system for recharging an implantable medical device having a rechargeable battery while the implantable medical device is implanted within a patient includes a recharge energy source configured to be disposed exterior to the patient and a recharging bridge configured to be implanted within the patient. The recharging bridge is configured to facilitate energy transfer from the recharge energy source to the implantable medical device.

20 Claims, 9 Drawing Sheets

(51) Int. Cl.
*A61N 1/375* (2006.01)
*H02J 7/02* (2016.01)
*H02J 50/12* (2016.01)
*H02J 50/50* (2016.01)
*A61N 1/39* (2006.01)
*H02J 50/10* (2016.01)

(52) U.S. Cl.
CPC .......... *A61N 1/37229* (2013.01); *H02J 7/025* (2013.01); *H02J 50/12* (2016.02); *H02J 50/50* (2016.02); *A61N 1/3956* (2013.01); *H02J 50/10* (2016.02)

(58) Field of Classification Search
CPC ............ A61N 1/37211; A61N 1/37217; A61N 1/37223; A61N 1/37229; A61N 1/37276; A61N 1/37288; A61N 1/3756; A61N 1/378; A61N 1/3787; A61B 2560/02; A61B 2560/0204; A61B 2560/0209; A61B 2560/0214; A61B 2560/0219
See application file for complete search history.

(56) References Cited

U.S. PATENT DOCUMENTS

| | | |
|---|---|---|
| 7,006,864 B2 | 2/2006 | Echt et al. |
| 7,050,849 B2 | 5/2006 | Echt et al. |
| 7,486,048 B2 | 2/2009 | Tsukamoto et al. |
| 7,515,967 B2 | 4/2009 | Phillips et al. |
| 8,290,600 B2 | 10/2012 | Hastings et al. |
| 8,594,806 B2 | 11/2013 | Cowley et al. |
| 9,072,911 B2 | 7/2015 | Hastings et al. |
| 9,531,195 B2 | 12/2016 | Thompson et al. |
| 2005/0075696 A1 | 4/2005 | Forsberg et al. |
| 2007/0049992 A1* | 3/2007 | Freeberg ............ A61N 1/37211 607/60 |
| 2007/0150019 A1* | 6/2007 | Youker ................ A61N 1/3787 607/29 |
| 2008/0021505 A1* | 1/2008 | Hastings .............. A61N 1/0587 607/9 |
| 2010/0105997 A1 | 4/2010 | Ecker et al. |
| 2011/0043051 A1* | 2/2011 | Meskens ............. H04B 5/0075 307/104 |
| 2011/0190842 A1 | 8/2011 | Johnson et al. |
| 2013/0079849 A1* | 3/2013 | Perryman .......... A61N 1/37223 607/60 |
| 2014/0213978 A1 | 7/2014 | Olson et al. |
| 2014/0340272 A1* | 11/2014 | Malewicki ............ H01Q 7/06 343/788 |
| 2015/0048790 A1* | 2/2015 | Rudser ................. A61N 1/3787 320/108 |
| 2015/0134024 A1 | 5/2015 | Sambelashvili et al. |
| 2015/0229134 A1 | 8/2015 | Masaoka et al. |
| 2015/0290379 A1 | 10/2015 | Rudser et al. |
| 2017/0271919 A1* | 9/2017 | Von Novak, III ...... H02J 50/10 |
| 2018/0185657 A1* | 7/2018 | LeBaron ............ A61N 1/36125 |

OTHER PUBLICATIONS

International Search Report and Written Opinion for Application No. PCT/US2018/025230, 13 pages, dated Jun. 11, 2018.

* cited by examiner

SYSTEM FOR RECHARGING A RECHARGEABLE IMPLANTABLE MEDICAL DEVICE INCLUDING AN IMPLANTABLE RECHARGING BRIDGE

CROSS REFERENCE TO RELATED APPLICATIONS

This application claims the benefit of U.S. Provisional Patent Application Ser. No. 62/480,772 filed on Apr. 3, 2017, the disclosure of which is incorporated herein by reference.

TECHNICAL FIELD

The present disclosure pertains to medical devices, and more particularly to implantable medical devices that are capable of delivering power to another implantable medical device.

BACKGROUND

Implantable medical devices are commonly used today to monitor physiological or other parameters of a patient and/or deliver therapy to a patient. In one example, to help patients with heart related conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In another example, neuro stimulators can be used to stimulate tissue of a patient to help alleviate pain and/or other condition. In yet another example, an implantable medical device may simply be an implantable monitor that monitors one or more physiological or other parameters of the patient, and communicates the sensed parameters to another device such as another implanted medical device or an external device. In some cases, two or more implantable medical devices are implanted within the same patient, sometimes working together to monitor and/or treat one or more conditions of the patient.

SUMMARY

The present disclosure pertains to medical devices, and more particularly to implantable medical devices that are capable of delivering power to another implantable medical device. In one example, a recharging bridge may be configured to be implanted within a patient in order to facilitate energy transfer from an exterior transmitter disposed exterior to the patient to an implantable medical device disposed at an implant site within the patient. The recharging bridge includes a receive coil, a transmit coil that is spaced from the receive coil and a connector for connecting the receive coil and the transmit coil such that inductive energy received by the receive coil is transferred to the transmit coil and re-transmitted by the transmit coil. The receive coil, the transmit coil and the connector are configured to be implantable within the patient such that the transmit coil is placed adjacent the implant site and the receive coil is placed adjacent the patient's skin.

Alternatively or additionally, the receive coil, the transmit coil and the connector may be configured such that the receive coil is placed within 1 cm of the patient's skin and the transmit coil is placed within 2 cm of the implant site.

Alternatively or additionally, the implant site may be within the patient's heart.

Alternatively or additionally, the implant site may be substernal.

Alternatively or additionally, the receive coil, the transmit coil and the connector has a resonance frequency that may be between 100 KHz and 10 MHz.

Alternatively or additionally, the receive coil may be electrically coupled to the transmit coil by two or more conductors.

Alternatively or additionally, the transmit coil may be spaced from the receive coil by about 1 to 10 cm.

Alternatively or additionally, the receive coil, the transmit coil and the connector may be supported by a common substrate.

Alternatively or additionally, the common substrate may be a flexible substrate.

Alternatively or additionally, each of the receive coil, the transmit coil and the connector may be formed, at least in part, by one or more traces on the common substrate.

Alternatively or additionally, the recharging bridge may further include one or more capacitors that are electrically coupled to one or more of the receive coil, the transmit coil and the connector.

Alternatively or additionally, the implantable medical device may be a leadless cardiac pacemaker (LCP) having a rechargeable battery, and the transmit coil of the recharging bridge may transmit inductive energy for recharge the rechargeable battery of the LCP.

Alternatively or additionally, the transmitter that is disposed exterior to the patient may include a transmitting coil that is configured to be held in place adjacent the receive coil of the recharging bridge when recharging the LCP.

In another example, a system may be configured for recharging an implantable medical device having a rechargeable battery while the implantable medical device is implanted within a patient. The system includes a recharge energy source that is configured to be disposed exterior to the patient and that includes a power source and a transmitting coil operably coupled to the power source such that the transmitting coil is able to transmit inductive power. The system includes a recharging bridge that is configured to facilitate energy transfer from the transmitting coil of the recharge energy source to the implantable medical device. The recharging bridge includes a receive coil configured to be implanted relatively nearer to the transmitting coil to receive inductive energy from the transmitting coil of the recharge energy source, a transmit coil configured to be implanted relatively nearer the implantable medical device and a connector operatively connecting the receive coil and the transmit coil of the recharging bridge such that inductive energy received by the receive coil from the transmitting coil of the recharge energy source is transferred to the transmit coil of the recharging bridge and re-transmitted by the transmit coil to the implantable medical device.

Alternatively or additionally, the recharge energy source may further include a controller that is coupled to the power source and to the transmitting coil, and that is configured to regulate operation of the transmitting coil.

Alternatively or additionally, the recharge energy source may further include a communications module operably coupled to the controller such that the controller can receive, via the communications module, information about a charge status of the rechargeable battery of the implantable medical device.

Alternatively or additionally, the implantable medical device may be configured to be implanted within the patient's heart.

Alternatively or additionally, the implantable medical device may include a device housing, a receive coil disposed relative to the device housing and the rechargeable battery. The implantable medical device includes recharge circuitry that is operably coupled to the receive coil of the implantable medical device and to the rechargeable battery, the recharge circuitry being configured to convert inductive energy received by the receive coil of the implantable medical device from the transmit coil of the recharging bridge into energy to recharge the rechargeable battery.

Alternatively or additionally, the receive coil of the recharging bridge may have a radius of about 0.1 to 2 cm, and the transmit coil of the recharging bridge may have a radius of about 0.1 to 2 cm, and the transmit coil is spaced from the receive coil by at about 1 to 10 cm.

In another example, a recharging bridge may be configured to be implanted within a patient in order to facilitate energy transfer from a transmitter to an implantable medical device disposed at an implant site within the patient. The recharging bridge includes a receive coil, a transmit coil that is spaced from the receive coil by about 1 to 10 cm and a connector for connecting the receive coil and the transmit coil such that inductive energy received by the receive coil is transferred to the transmit coil and re-transmitted by the transmit coil. The receive coil, the transmit coil and the connector are configured to be implantable within the patient such that the transmit coil is placed within 2 cm of the implant site and the receive coil is placed within 1 cm of the patient's skin.

The above summary of some illustrative embodiments is not intended to describe each disclosed embodiment or every implementation of the present disclosure. The Figures, and Description, which follow, more particularly exemplify some of these embodiments.

BRIEF DESCRIPTION OF THE DRAWINGS

The disclosure may be more completely understood in consideration of the following description in connection with the accompanying drawings, in which.

Figure 1:
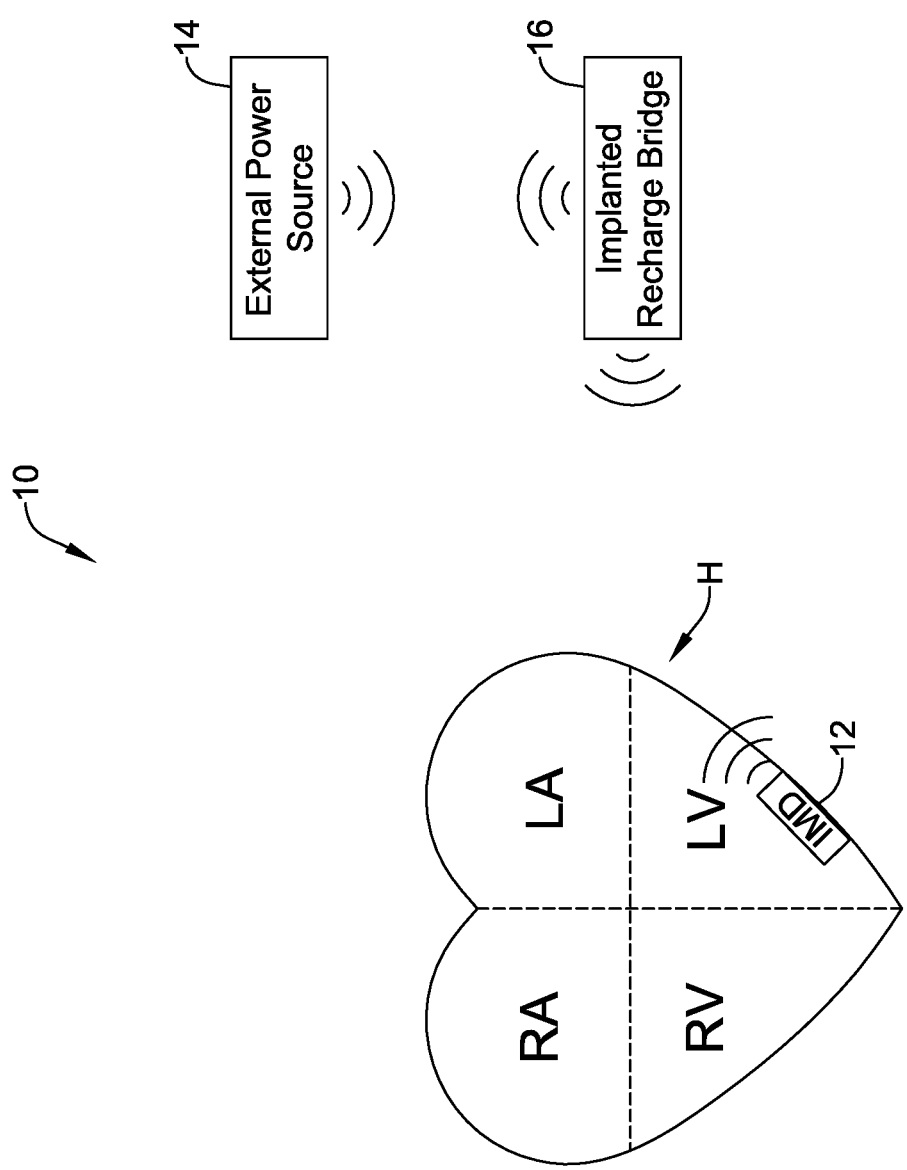
FIG. 1 is a schematic block diagram of a system including an implantable medical device (IMD), an external power source and an implantable recharge bridge in accordance with an example of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure. While the present disclosure is applicable to any suitable implantable medical device (IMD), the description below often uses implantable cardioverter-defibrillator (ICD) and/or pacemakers as particular examples.

FIG. 1 is a schematic diagram showing an illustrative system 10 that may be used to sense and/or pace a heart H. In some cases, the system 10 may also be configured to shock the heart H. The heart H includes a right atrium RA and a right ventricle RV. The heart H also includes a left atrium LA and a left ventricle LV. In some cases, the system 10 may include a medical device that provides anti-arrhythmic therapy to the heart H. In some cases, the system 10 may include an implantable medical device (IMD) 12 that may be deployed near or even within the heart H. The implanted location of the IMD 12 may be considered as being an implant site. As illustrated, the IMD 12 is shown in the left ventricle LV. This is merely illustrative, as the IMD 12 may be implanted within any other chamber of the heart H.

In some cases, as will be discussed, the IMD 12 may include a power supply such as a rechargeable battery or a capacitor that provides power for operation of the IMD 12 yet may require periodic charging or recharging in order to have sufficient power to continue to power operation of the IMD 12. In some cases, for example, the system 10 may include an external power source 14 that is configured to transmit energy into the patient that can be harnessed by the IMD 12 and used to recharge its power supply. In some instances, in order to improve the efficiency of power transmission from the external power source 14 to the IMD 12, the system 10 may include an implanted recharge bridge 16. In some cases, the implanted recharge bridge 16 may receive energy transmitted by the external power source 14 and transmit the energy to the IMD 12.

Figure 2:
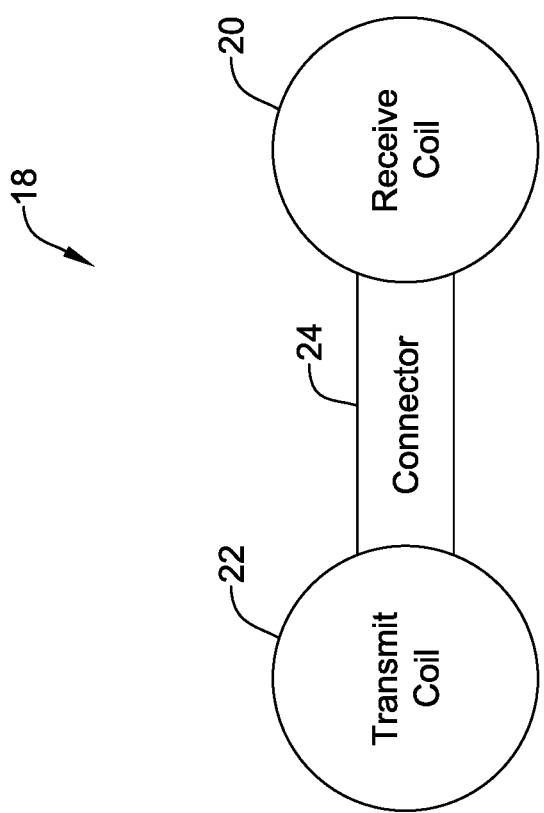
FIG. 2 is a schematic diagram of an implantable recharge bridge usable in the system of FIG. 1 in accordance with an example of the disclosure.

FIG. 2 is a schematic diagram of a recharging bridge 18 that is configured to be implanted within a patient in order to facilitate energy transfer from an exterior transmitter (such as may be included in the external power source 14) to the IMD 12 that is disposed at an implant site (such as but not limited to near or within the heart H). The recharging bridge 18 may be considered as being an example of the implanted recharge bridge 16 shown in FIG. 1. The recharging bridge 18 includes a receive coil 20 and a transmit coil 22 that is spaced from the receive coil 20. A connector 24 extends between the receive coil 20 and the transmit coil 22, and physically connects the receive coil 20 and the transmit coil 22. The connector 24 may include electrical connectors that electrically connect the receive coil 20 and the transmit coil 22 such that inductive energy received by the receive coil 20 may be transferred to the transmit coil 22 and re-transmitted by the transmit coil 22. The receive coil 20, the transmit coil 22 and the connector 24 are all configured to be implantable within the patient such that the transmit coil 22 is placed adjacent the implant site and the receive coil 20 is placed adjacent the patient's skin. In some cases, the receive coil 20, the transmit coil 22 and the connector 24 has a resonance frequency that is between 100 KHz and 10 MHz.

In some cases, for example, the IMD 12 (FIG. 1) may be a leadless cardiac pacemaker (LCP) that includes a rechargeable battery, and the transmit coil 22 may transmit inductive energy for recharge the rechargeable battery of the LCP. In some cases, the external power source 14 (FIG. 1) may include a transmitting coil that is configured to be held in place adjacent the receive coil 20 when recharging the LCP. For example, the external power source 14 may be held in place on the exterior of the patient's chest, as close as possible to where the receive coil 20 is located.

In some cases, for example, the receive coil 20, the transmit coil 22 and the connector 24 are configured such that the receive coil 20 is placed within 3 centimeters (cm), within 2 cm or less than 2 cm from the patient's skin and the transmit coil 22 is placed within 5 cm, within 4 cm, within 3 cm or less than 3 cm from the implant site. In some instances, the recharging bridge 18 may be configured to place the receive coil 20 within 1 cm of the patient's skin and to place the transmit coil 22 within 2 cm of the implant site. In some instances, the connector 24 may be configured to space the transmit coil 22 about 1 to 10 cm away from the receive coil 20, or in some cases, at least 5 cm away from the receive coil 20. In some cases, the receive coil 20 may have a radius of about 0.1 to 2 cm, or a radius of about 1 cm. In some cases, the transmit coil 22 may have a radius of about 0.1 to 2 cm, or a radius of about 1 cm. In some cases, the implant site may be within the patient's heart H. In some cases, the implant site may be substernal.

Figure 3:
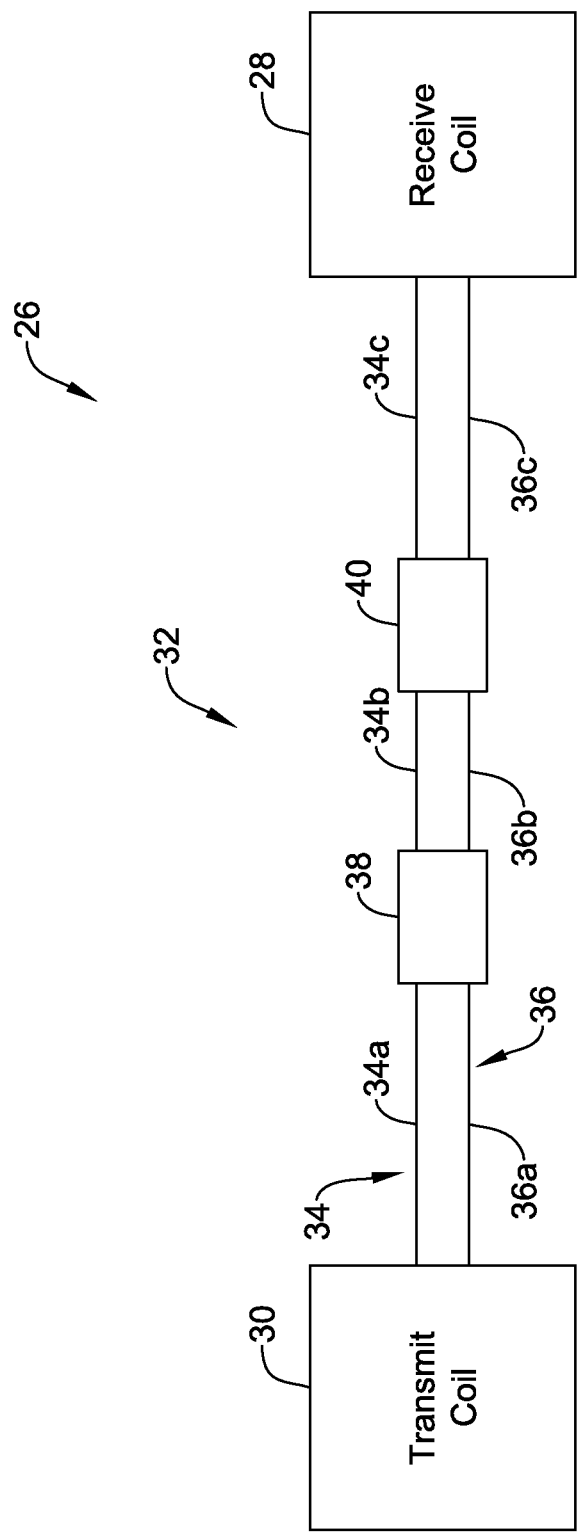
FIG. 3 is a schematic diagram of an implantable recharge bridge usable in the system of FIG. 1 in accordance with an example of the disclosure.

FIG. 3 is a schematic diagram of a recharging bridge 26 that is configured to be implanted within a patient in order to facilitate energy transfer from an exterior transmitter (such as may be included in the external power source 14) to the IMD 12 that is disposed at an implant site (such as but not limited to near or within the heart H). The recharging bridge 26 may be considered as being an example of the implanted recharge bridge 16 shown in FIG. 1. The recharging bridge 26 includes a receive coil 28 and a transmit coil 30 that is spaced from the receive coil 28. The recharging bridge 26 includes a connecting structure 32 that mechanically and electrically couples the receive coil 28 and the transmit coil 30. In some cases, the connecting structure 32 includes a first conductor 34 and a second conductor 36 that electrically couple the receive coil 28 to the transmit coil 30. In some cases, the connecting structure 32 includes capacitors 38, 40 that can be used to temporarily store received energy before transmitting. While two capacitors 38, 40 are illustrated, it will be appreciated that there may be a single capacitor, or three or more capacitors. In some cases, the capacitors 38, 40 divide the first conductor 34 into segments 34*a*, 34*b*, 34*c* and divide the second conductor 36 into segments 36*a*, 36*b*, 36*c*.

Figure 4:
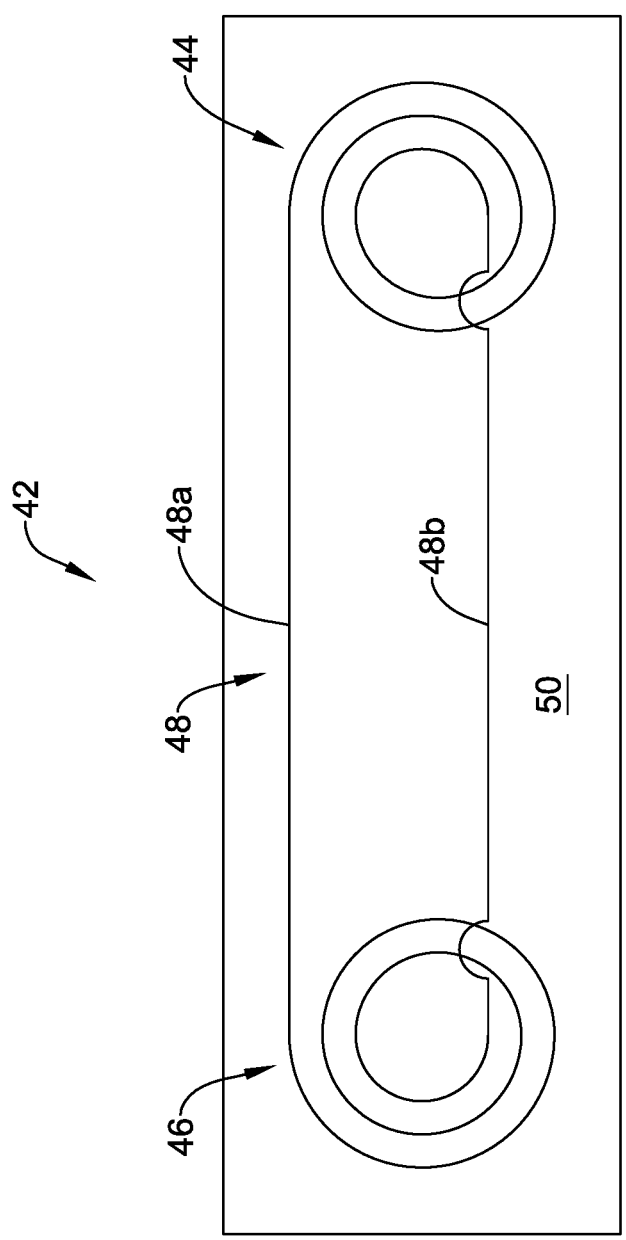
FIG. 4 is a schematic diagram of an implantable recharge bridge usable in the system of FIG. 1 in accordance with an example of the disclosure.

FIG. 4 is a schematic diagram of a recharging bridge 42 that is configured to be implanted within a patient in order to facilitate energy transfer from an exterior transmitter (such as may be included in the external power source 14) to the IMD 12 that is disposed at an implant site (such as but not limited to near or within the heart H). The recharging bridge 42 may be considered as being an example of the implanted recharge bridge 16 shown in FIG. 1. The recharging bridge 42 includes a receive coil 44 and a transmit coil 46. A connector 48 including a first electrical connector 48*a* and a second electrical connector 48*b* extend between the receive coil 44 and the transmit coil 46, electrically coupling the receive coil 44 and the transmit coil 46. In some cases, the receive coil 44, the transmit coil 46 and the connector 48 are supported by a common substrate 50. In some instances, the common substrate 50 may be flexible. In some cases, each of the receive coil 44, the transmit coil 46 and the connector 48 may be formed, at least in part, by one or more traces on the common substrate 50.

Figure 5:
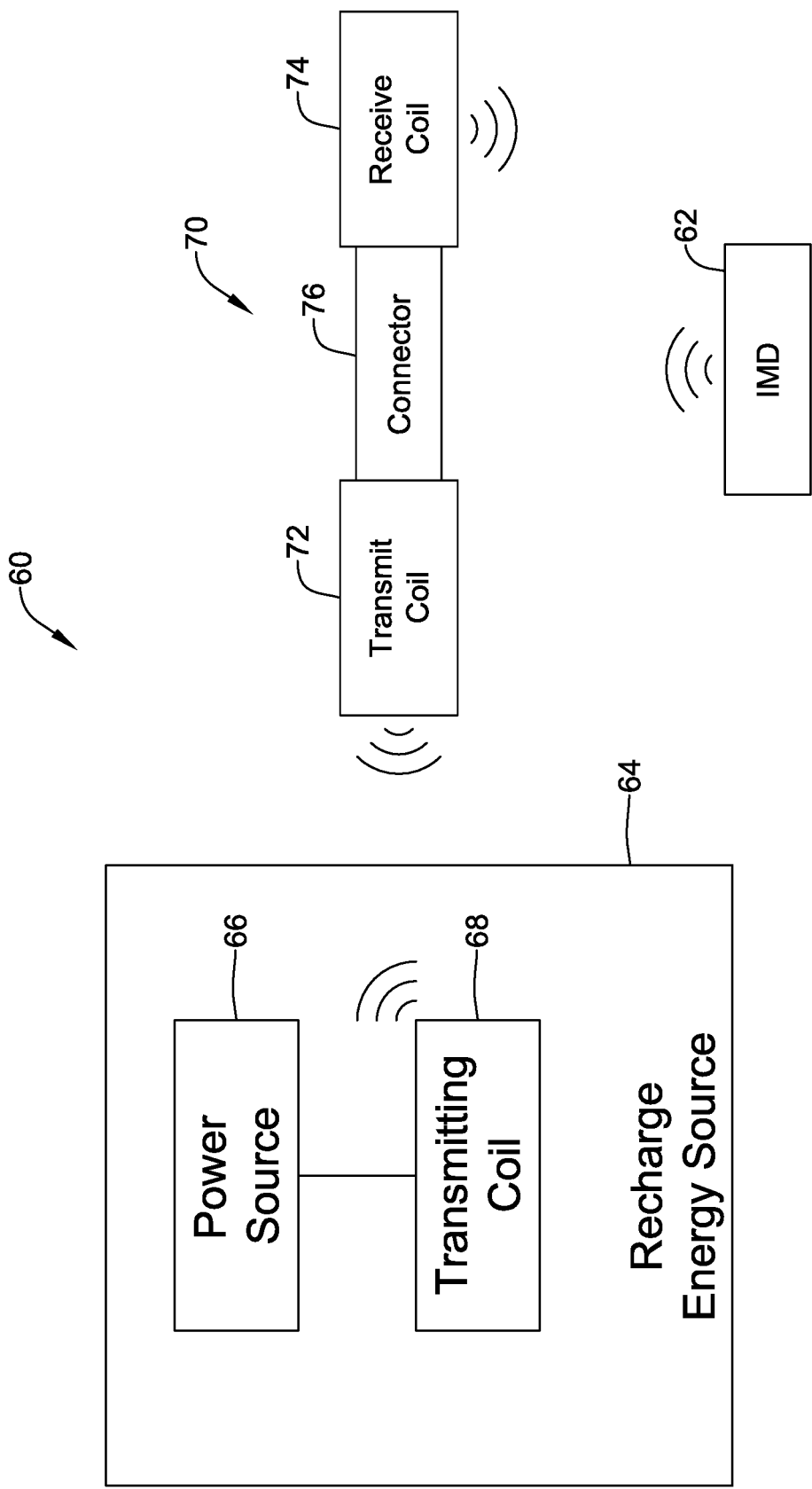
FIG. 5 is a schematic block diagram of a system including an implantable medical device (IMD), a recharge power source and a recharge bridge in accordance with an example of the disclosure.

FIG. 5 is a schematic block diagram of a system 60 for recharging an implantable medical device (IMD) 62 having a rechargeable battery while the implantable medical device is implanted within a patient. The system 60 includes a recharge energy source 64 that is configured to be disposed exterior to the patient. In some cases, the recharge energy source 64 includes a power source 66 and a transmitting coil 68 that is operably coupled to the power source 66 such that the transmitting coil 68 is able to transmit inductive power. In some cases, for example, the recharge energy source 64 may be configured to be able to be placed and/or held proximate the patient's chest while recharging the rechargeable battery within the IMD 62.

The system 60 also includes a recharging bridge 70 that is configured to facilitate energy transfer from the transmitting coil 68 of the recharge energy source 64 to the IMD 62. In some cases, any of the recharging bridge 18 (FIG. 2), the recharging bridge 26 (FIG. 3) or the recharging bridge 42 (FIG. 4) may be used as the recharging bridge 70. In some cases, the recharging bridge 70 may combine features of these recharging bridges, 18, 26, 42.

The recharging bridge 70 includes a receive coil 72 that is configured to be implanted relatively nearer to the transmitting coil 68 to receive inductive energy from the transmitting coil 68 of the recharge energy source 64 and a transmit coil 74 that is configured to be implanted relatively nearer the IMD 62. A connector 76 operatively connects the receive coil 72 and the transmit coil 74 such that inductive energy received by the receive coil 72 from the transmitting coil 68 of the recharge energy source 64 is transferred to the transmit coil 74 of the recharging bridge 70 and re-transmitted by the transmit coil 72 to the IMD 62.

Figure 6:
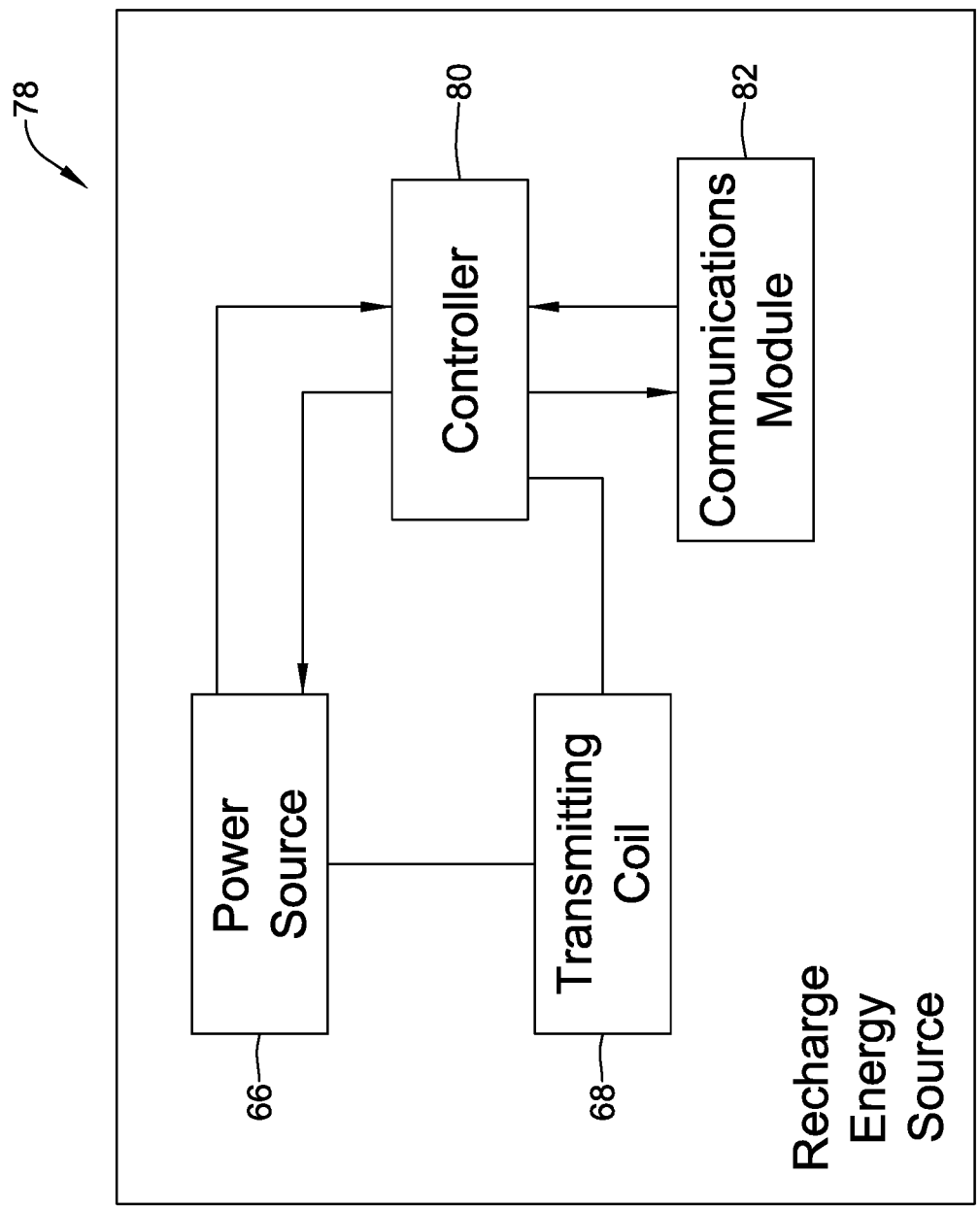
FIG. 6 is a schematic block diagram of a recharge power source useable in the system of FIG. 5 in accordance with an example of the disclosure.

FIG. 6 is a schematic block diagram of a recharge energy source 78 that may be used in the system 60. The recharge energy source 78 includes the power source 66 and the transmitting coil 68 as discussed with respect to FIG. 5. In some cases, the recharge energy source 78 may include a controller 80 that is coupled to the power source 66 and to the transmitting coil 68 and that is configured to regulate operation of the transmitting coil 68. In some cases, the recharge energy source 78 may also include a communications module 82 that is operably coupled to the controller 80 such that the controller 80 can receive, via the communications module 82, information about a charge status of the rechargeable battery of the IMD 62. For example, in some cases, the IMD 62 may transmit a request for power. In some instances, the IMD 62 may simply periodically transmit an indication of its current battery status, and the controller 80 may be configured to determine when to transmit power to the IMD 62 based on the current battery status.

Figure 7:
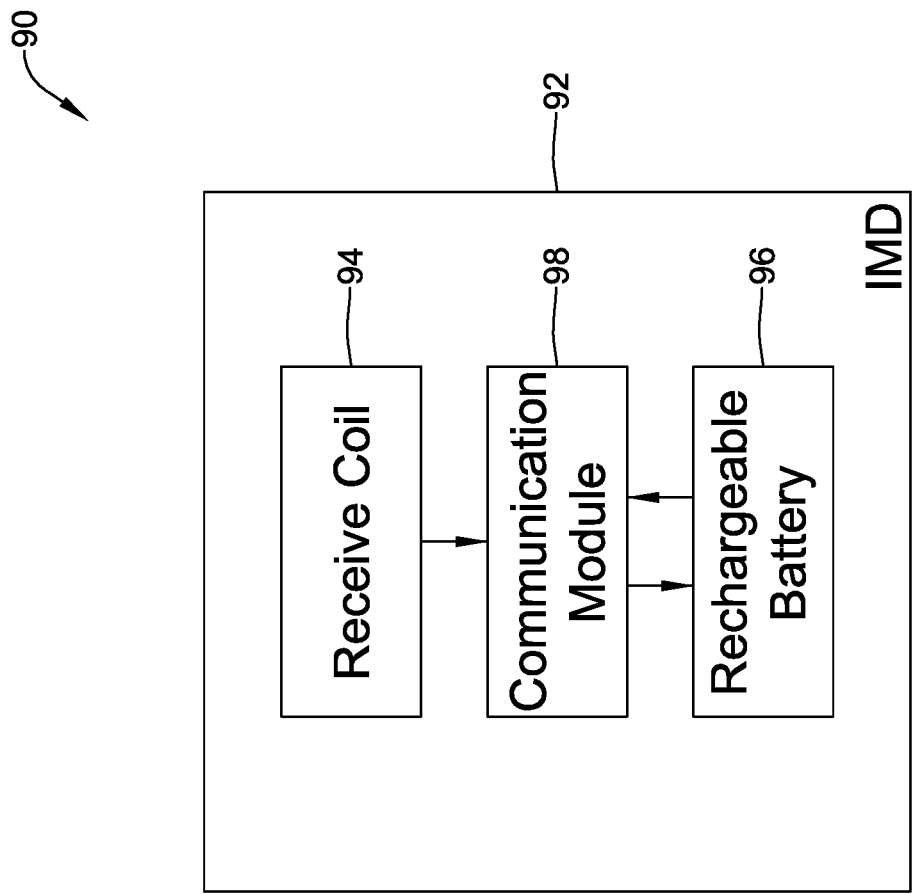
FIG. 7 is a schematic block diagram of an implantable medical device (IMD) usable in the system of FIG. 5 in accordance with an example of the disclosure.

FIG. 7 is a schematic block diagram of an implantable medical device (IMD) 90 that may be considered as being an example of the IMD 12 (FIG. 10 or the IMD 62 (FIG. 6). In some cases, the IMD 90 includes a device housing 92 and a receive coil 94 that is disposed relative to the device housing 92. A rechargeable battery 96 is disposed within the device housing 92. The IMD 90 includes recharge circuitry 98 that is operably coupled to the receive coil 94 and to the rechargeable battery 96. In some cases, the recharge circuitry 98 may be configured to convert inductive energy received by the receive coil 94 from the transmit coil of the recharging bridge into energy to recharge the rechargeable battery 96.

Figure 8:
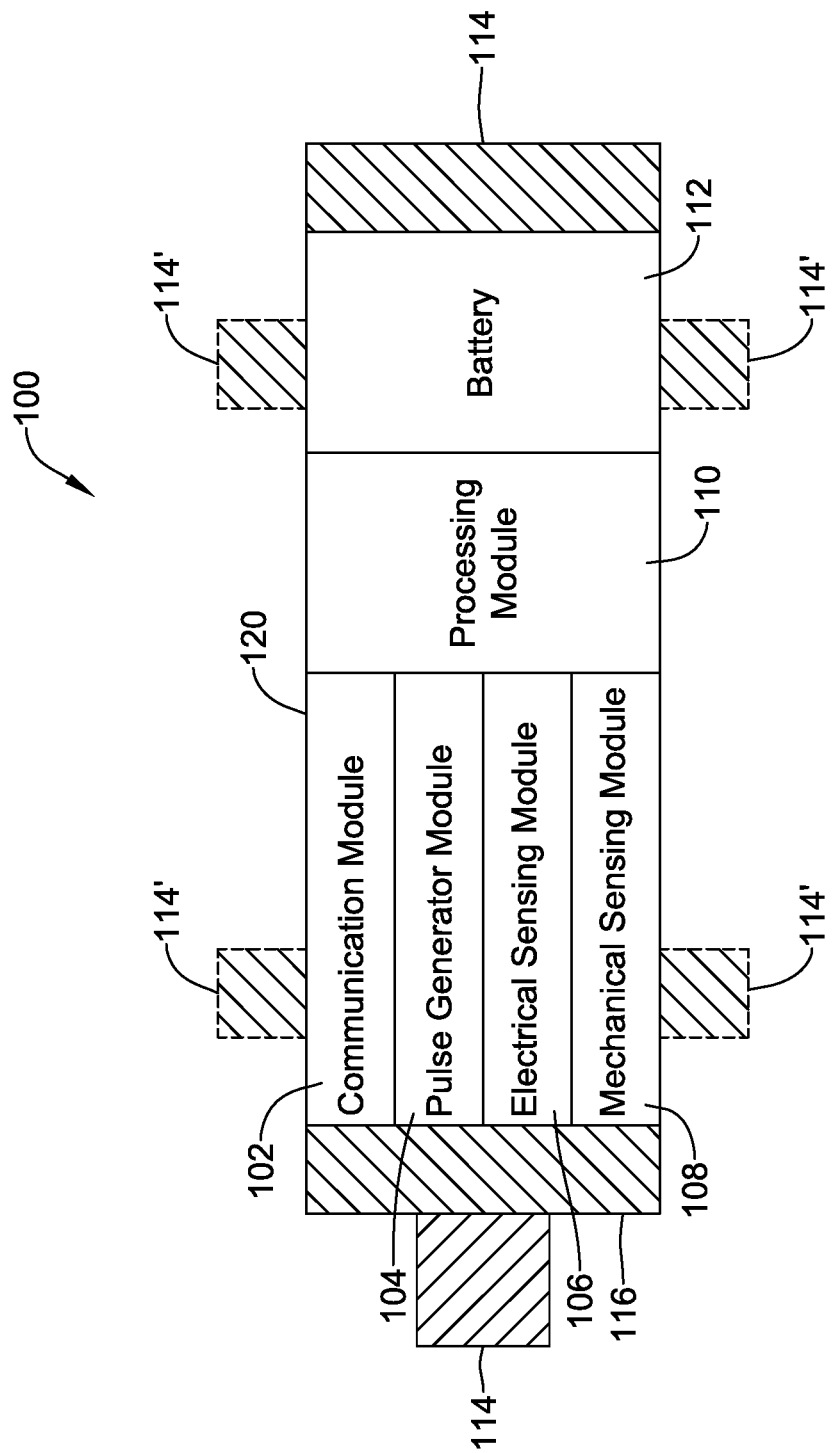
FIG. 8 is a schematic block diagram of an illustrative IMD in accordance with an example of the disclosure.

FIG. 8 depicts an illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 8, the LCP 100 may be a compact device with all components housed within the or directly on a housing 120. In some cases, the LCP 100 may be considered as being an example of the IMD 12 (FIG. 1) or the IMD 62 (FIG. 5). In the example shown in FIG. 8, the LCP 100 may include a communication module 102, a pulse generator module 104, an electrical sensing module 106, a mechanical sensing module 108, a processing module 110, a battery 112, and an electrode arrangement 114. The LCP 100 may also include a receive coil for receiving inductive power, and a recharge circuit for recharging the battery 112 (or capacitor) using the received inductive power. It is contemplated that the LCP 100 may include more or fewer modules, depending on the application.

The communication module 102 may be configured to communicate with devices such as sensors, other medical devices such as an SICD, another LCP, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 8, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy. In some cases, the pulse generator 104 may provide a controllable pulse energy. In some cases, the pulse generator 104 may allow the controller to control the pulse voltage, pulse width, pulse shape or morphology, and/or any other suitable pulse characteristic.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 8 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. A recharge circuit may receive power from a receiving coil of the LCP 100, and use the received power to recharge the rechargeable battery. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 9:
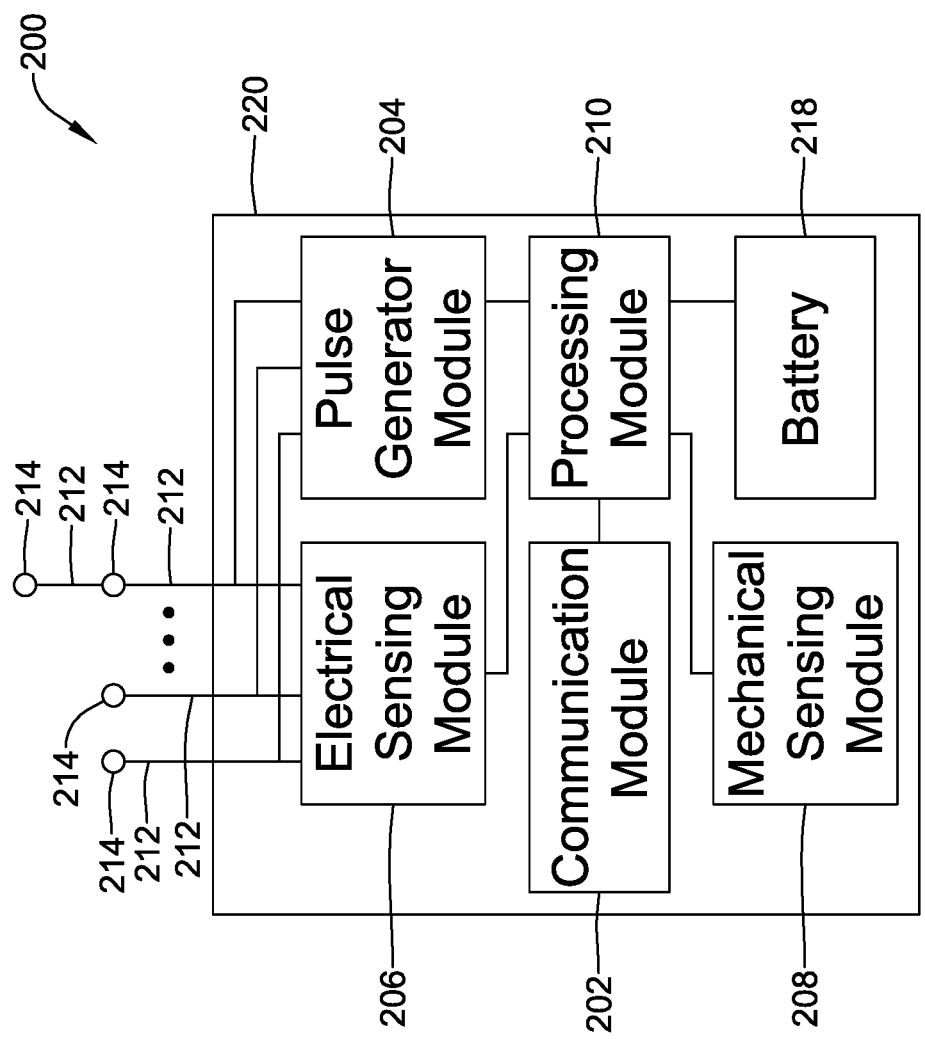
FIG. 9 is a schematic block diagram of another illustrative medical device that may be used in conjunction with the IMD of FIG. 8.

FIG. 9 depicts an example of another or second medical device (MD) 200, which may be used in conjunction with the LCP 100 (FIG. 8) in order to detect and/or treat cardiac abnormalities. In some cases, the MD 200 may be considered as an example of the IMD 12 (FIG. 1) or the IMD 62

(FIG. 5) and may for example represent an implantable cardioverter defibrillator (ICD) or a subcutaneous implantable cardioverter defibrillator (SICD). In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 8, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly). In some cases, a transmit coil may be supported by the lead, such at a location along the length of the lead that is near the receive coil of a remote implantable medical device.

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD) with the ability to pace. In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD) with the ability to pace. In examples where the MD 200 is an S-ICD, one of the leads 212 may be a subcutaneously implanted lead. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart H.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy. In some cases, the MD 200 may be external to the patient's body may include a lead that extends transvenously into the heart. The lead may be used to sense and/or pace the heart. A transmit coil may be placed on the lead and adjacent to or inside of the heart.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A recharging bridge configured to be implanted within a patient in order to facilitate energy transfer from an exterior transmitter disposed exterior to the patient to an implantable medical device disposed at an implant site within the patient, the recharging bridge comprising:
   a receive coil;
   a transmit coil spaced from the receive coil;
   a connector for connecting the receive coil and the transmit coil such that inductive energy received by the receive coil induces a current in the receive coil that is transferred directly to the transmit coil through one or more conductive paths of the connector, which causes the transmit coil to re-transmit at least part of the inductive energy received by the receive coil; and the receive coil, the transmit coil and the connector are configured to be implantable within the patient, such that the transmit coil is configured to be placed adjacent the implant site and the receive coil is configured to be placed adjacent the patient's skin, wherein the connector is configured to allow the transmit coil to be spaced from the receive coil by at least 1 centimeter.

2. The recharging bridge of claim 1, wherein the recharge bridge is free from any power amplifiers operatively coupled between the receive coil and the transmit coil of the recharge bridge.

3. The recharging bridge of claim 1, wherein the receive coil, the transmit coil and the connector are supported by a common substrate.

4. The recharging bridge of claim 3, wherein the common substrate is a flexible substrate.

5. The recharging bridge of claim 3, wherein each of the receive coil, the transmit coil and the connector are formed, at least in part, by one or more traces on the common substrate.

6. The recharging bridge of claim 3, further comprising one or more capacitors electrically coupled to one or more of the receive coil, the transmit coil and the connector.

7. The recharging bridge of claim 1, wherein the receive coil, the transmit coil and the connector has a resonance frequency, and wherein the resonance frequency is between 100 KHz and 10 MHz.

8. The recharging bridge of claim 1, wherein the receive coil is electrically coupled to the transmit coil by two or more conductors.

9. The recharging bridge of claim 1, wherein the implantable medical device comprises a leadless cardiac pacemaker (LCP) having a rechargeable battery, and the transmit coil of the recharging bridge transmits inductive energy for recharging the rechargeable battery of the LCP.

10. The recharging bridge of claim 9, wherein the transmitter disposed exterior to the patient comprises a transmitting coil, and the transmitting coil is configured to be held in place adjacent the receive coil of the recharging bridge when recharging the LCP.

11. The recharging bridge of claim 1, wherein the receive coil, the transmit coil and the connector are configured such that the receive coil is placed within 1 cm of the patient's skin and the transmit coil is placed within 2 cm of the implant site.

12. The recharging bridge of claim 11, wherein the implant site is within the patient's heart.

13. The recharging bridge of claim 11 wherein the implant site is substernal.

14. A system for recharging an implantable medical device having a rechargeable battery while the implantable medical device is implanted within a patient, the system comprising:

a recharge energy source configured to be disposed exterior to the patient, the recharge energy source comprising:
  a power source; and
  a transmitting coil operably coupled to the power source such that the transmitting coil is able to transmit inductive power; and a recharging bridge configured to facilitate energy transfer from the transmitting coil of the recharge energy source to the implantable medical device, the recharging bridge comprising:
  a receive coil configured to be implanted relatively nearer to the transmitting coil to receive inductive energy from the transmitting coil of the recharge energy source;
  a transmit coil configured to be implanted relatively nearer the implantable medical device; and
  a connector operatively connecting the receive coil and the transmit coil of the recharging bridge such that inductive energy received by the receive coil from the transmitting coil of the recharge energy source induces a current in the receive coil that is transferred directly to the transmit coil of the recharging bridge through one or more conductive paths of the connector, which causes the transmit coil of the recharging bridge to re-transmit at least part of the inductive energy received by the receive coil to the implantable medical device, and wherein the connector is configured to allow the transmit coil of the recharging bridge to be spaced from the receive coil of the recharging bridge by at least 1 centimeter.

15. The system of claim 14, wherein the receive coil of the recharging bridge has a radius of about 1 centimeter, and the transmit coil of the recharging bridge has a radius of about 1 centimeter, and the transmit coil is spaced from the receive coil by 1 to 10 cm.

16. The system of claim 14, wherein the recharge energy source further comprises a controller that is coupled to the power source and to the transmitting coil, and that is configured to regulate operation of the transmitting coil.

17. The system of claim 16, wherein the recharge energy source further comprises a communications module operably coupled to the controller such that the controller can receive, via the communications module, information about a charge status of the rechargeable battery of the implantable medical device.

18. The system of claim 14, wherein the implantable medical device is configured to be implanted within the patient's heart.

19. The system of claim 14, wherein the implantable medical device comprises:
  a device housing;
  a receive coil disposed relative to the device housing;
  the rechargeable battery; and
  recharge circuitry operably coupled to the receive coil of the implantable medical device and to the rechargeable battery, the recharge circuitry configured to convert inductive energy received by the receive coil of the implantable medical device from the transmit coil of the recharging bridge into energy to recharge the rechargeable battery.

20. A recharging bridge configured to be implanted within a patient in order to facilitate energy transfer from a transmitter to an implantable medical device disposed at an implant site within the patient, the recharging bridge comprising:
  a receive coil;
  a transmit coil spaced from the receive coil by 1 to 10 cm;
  a connector for connecting the receive coil and the transmit coil such that inductive energy received by the receive coil induces a current in the receive coil that is directly transferred to the transmit coil through one or more conductive paths of the connector, which causes the transmit coil to re-transmit at least part of the inductive energy received by the receive coil; and the receive coil, the transmit coil and the connector are configured to be implantable within the patient such that the transmit coil is placed within 2 cm of the implant site and the receive coil is placed within 1 cm of the patient's skin.

* * * * *